United States Patent [19]

Ayotte et al.

[11] 4,349,275

[45] Sep. 14, 1982

[54] SLIDE HOLDER FOR SPINNER

[75] Inventors: Gary A. Ayotte, Newtonville; Jules J. Boh, Framingham; Thomas G. Breen, Fitchburg, all of Mass.

[73] Assignee: Coulter Electronics, Inc., Hialeah, Fla.

[21] Appl. No.: 160,963

[22] Filed: Jun. 19, 1980

[51] Int. Cl.³ .................... G01N 1/28; G01N 21/34
[52] U.S. Cl. ........................... 356/36; 118/52;
118/500; 233/26; 356/244; 422/104; 427/2; 427/4
[58] Field of Search ............... 233/26; 422/72, 104;
427/2, 4; 118/52, 53, 54, 500; 356/36

[56] References Cited

U.S. PATENT DOCUMENTS 3,705,048  12/1972  Staunton ...................... 422/104
4,103,643   8/1978  Staunton ...................... 118/52

Primary Examiner—Michael S. Marcus
Attorney, Agent, or Firm—Gerald R. Hibnick

[57] ABSTRACT

Disclosed is a substrate holder and method of holding a substrate for a spinner apparatus wherein the holder has a first pair of diagonally positioned locking members under which the substrate is locked during acceleration of the rotating holder and a second pair of diagonally positioned locking members under which the substrate is locked during deceleration of the holder.

10 Claims, 3 Drawing Figures

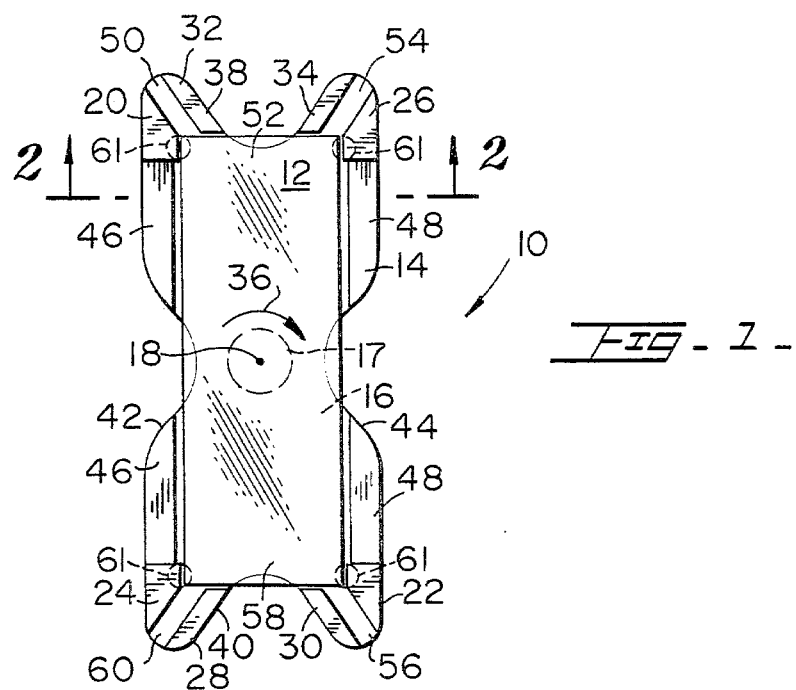
Fig. 1
Fig. 2
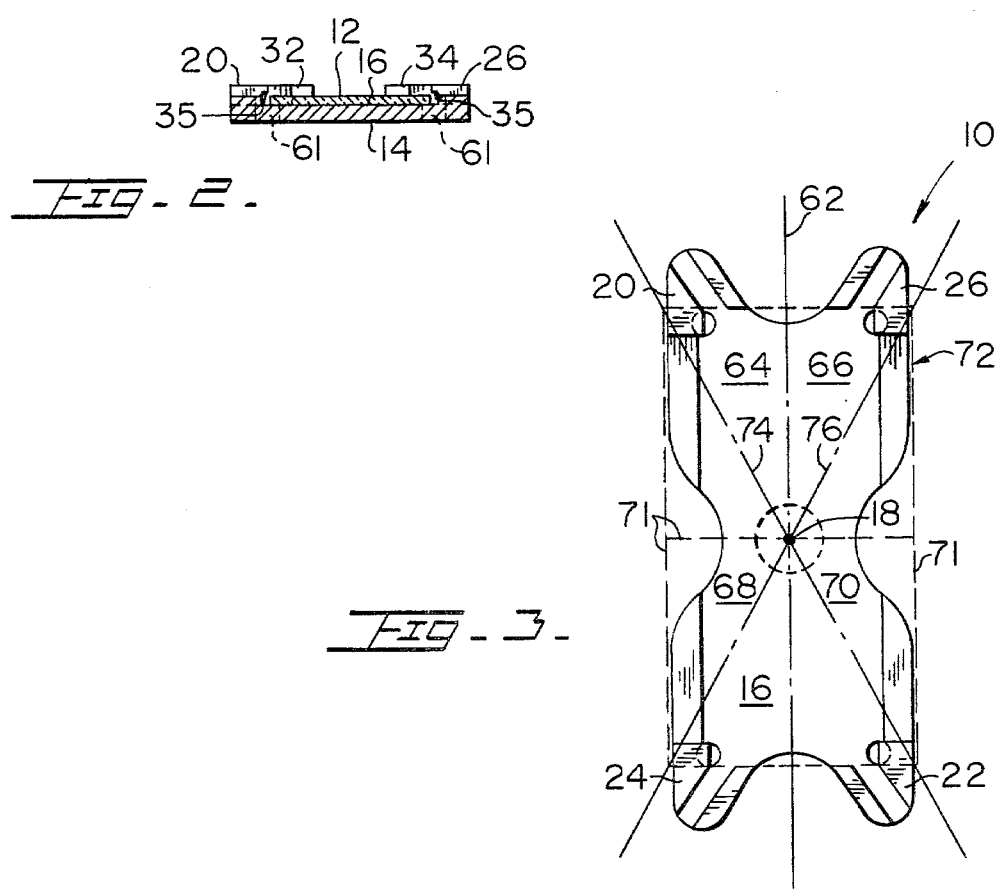
Fig. 3

SLIDE HOLDER FOR SPINNER

BACKGROUND OF THE INVENTION

The invention relates to slide holders for securing blood smear slides during spinning.

THE DESCRIPTION OF THE PRIOR ART

Monolayers of cells have been prepared for subsequent analysis by a number of techniques. The preferred method for automated differential analysis is spinning. A microscope slide is put on the slide holder of an apparatus, designed to spin the slide for about 0.3 to 2.5 seconds at 2,500 to 5,500 RPM. The exact values chosen depend on the torque of the motor available, i.e., acceleration; the red cell count of the blood sample to be used; the final cell density desired; and like factors. The blood is deposited in the center of the slide and the cycle initiated. The spinner will rapidly accelerate the slide, spinning it horizontally around its geometric center, and then decelerate again. A typical workload of a hospital may consist of more than 250 slides/day. It becomes apparent that it is important to have a convenient and effortless way of putting slides in and taking them out again.

Apparatuses commercially available try to solve the problem of holding slides in one of three ways. First, the slide has been held by means of spring loaded clamps, as illustrated in U.S. Pat. No. 3,906,890 to Amos et al. The disadvantage of this technique is that the spring pressure has to be overcome by the operator every time a slide is inserted or taken out; hence, slowing down the slide processing. Secondly, the slide has been held by use of a partial pressure, as shown by U.S. Pat. No. 3,848,962 to Nelson. This arrangement utilizes a vacuum pump, a valve and a rotary seal to accomplish the holding of the slide, which adds complexity, weight, cost, and reduces reliability of the system. Third, the slide is put in the center of a circular slide holder in a recess, without active means of securing it there, as shown in U.S. Pat. No. 3,906,890 to Amos et al. With this technique, a certain percentage of the slides will not remain in place but will be broken and shattered with the concomitant possibility of injury to the operator and damage to the spinner by small glass fragments, which also present a biological hazard due to the blood samples involved.

SUMMARY OF THE INVENTION

The invention is directed toward a substrate holder to be used in a spinner apparatus for creating spun blood smear substrates and toward a method of holding the substrate during the spinning operation. The substrate holder comprises a base portion for supporting the substrate, having mounted thereon a first pair of diagonally-opposed first locking members and a second pair of diagonally-opposed locking members. The substrate is placed within the confines of the locking members. As the substrate holder is accelerated, the inertia of the substrate will cause it to lock under the first pair of locking members. As the substrate is decelerated, the inertia of the substrate causes it to free itself from the first pair of locking members and to lock under the second pair of locking members.

The slide holder according to the invention allows for the operator to insert and take out slides by merely dropping them in place and by taking them out, without the need to overcome spring tension, to have careful alignment and like hinderances of the prior art devices. Moreover, the substrate holder can be manufactured as a single piece, for example from plastic, resulting in significant cost reduction, simplicity and improved reliability.

DESCRIPTION OF THE DRAWINGS

Further objects and advantages of the present invention will become apparent as the following description proceeds, taken in conjunction with the accompanying drawing in which:

FIG. 1 is a top view of the substrate holder according to the invention,

FIG. 2 is a cross-sectional view of the substrate holder taken along section line 2—2 in FIG. 1, and FIG. 3 is a top view of the substrate holder with a geometric map superimposed thereover.

DETAILED DESCRIPTION OF THE PREFERRED EMBODIMENT

Referring to FIG. 1, there is disclosed a substrate holder, generally referred to by numeral 10, having a microscope slide or like substrate 12 positioned therein. The substrate holder 10 is used in a spinner or centrifuge unit of the type wherein spun blood smear substrates are formed, such as the spinner disclosed in U.S. Pat. No. 4,016,828 to Maher, Jr. et al.

The substrate holder 10 has a mounting base problem 14 with an upward facing, planar surface 16 for receiving and supporting the substrate 12. In a conventional manner, the substrate holder 10 is supported by a shaft 17 for rotational motion of the substrate 12 about a rotational axis 18 of the shaft 17. A suitable, motor driven shaft arrangement is shown in the centrifuge unit of the previously mentioned U.S. Pat. No. 4,016,828.

The substrate holder 10 has a first pair of diagonally-opposed locking members 20 and 22 and a second pair of diagonally-opposed locking members 24 and 26. A first pair of adjacent studs 28 and 30 and a second pair of adjacent studs 32 and 34 are mounted in protruding relationship to the base portion 14, the first and second pairs being positioned at opposed, short ends of the base portion 14.

Referring to FIGS. 1 and 2, each of the locking members 20, 22, 24 and 26 have a inwardly-extending overhang portion 35. Each of the studs 28, 30, 32 and 34 protrude upward from the planar surface 16.

For the purposes of illustrating the operation of the substrate holder 10, it will be assumed that the substrate holder 10 will rotate in the plane of the paper in the direction of a rotation-indicating arrow 36. First, the operator drops the slide in place on the planar surface 16. Since the spacing between adjacent locking members 20, 26 and 22, 24 is greater than the width dimensions of the substrate 12, the substrate 12 can be maintained in a horizontal disposition while being put in place. As the substrate holder 10 is accelerated in the direction of the arrow 36, the inertia of the substrate 12 causes the substrate 12 to pivot with respect to the substrate holder 10 so as to slide under and be secured under the overhang portions 35 of the locking members 20 and 22. Hence, the locking members define means for securing the edge of the substrate 12 to prevent the substrate from flying up during spinning. The studs 28 through 34 are sufficiently spaced-apart from the ends of the substrate 12 to allow substrate 12 to slide into the locking members 20 and 22, while preventing the substrate 12 from slipping out of one of the short ends of the substrate holder 10. More importantly, the studs provide proper end-to-end alignment of the substrate 12 so that the locking members are cooperatively aligned with the longitudinal edges of the substrate 12. The engagement of the substrate 12 with the locking members 20 and 22 during acceleration allows for the substrate 12 to be secured during a spin cycle of the centrifuge unit. As the substrate holder 10 decelerates at the end of the spin cycle, the substrate frees itself from its engagement with the locking members 20 and 22 and, due to its inertia, pivots in the direction of the arrow 36 to slide under the locking members 24 and 26.

The slide holder 10 can be manufactured as a single piece, for example, from plastic. Although four locking members 20 through 26 are shown, it will be obvious to those skilled in the art, that locking members 20 and 24 can be joined and locking members 22 and 26 can be joined; thereby forming only two locking members, each of which would extend along the majority of one of the longitudinal edges of the substrate holder 10. Likewise, although the studs 28 through 34 are shown in pairs at the short ends of the substrate holder 10, the adjacent studs could be joined to define a single stud at each end of the substrate holder 10.

Preferably, but not necessarily, a pair of opposed recesses 38 and 40 are formed in the short ends of the base portion 14 and a pair of opposed recesses 42 and 44 are formed in the lateral sides of the base portion 14 so as to allow the substrate 12 to overlap the base portion 14. By virtue of this overlapping relationship, the substrate 12 can be readily dropped in and removed from the substrate holder 10. Preferably, but not necessarily, the lateral edges can be raised to define two opposed ledges 46 and 48, having straight edges spaced-apart slightly from the substrate 12 when it is centered. The ledges 46 and 48 rise to a height approximately that of the thickness of the substrate 12 so as to provide an aerodynamic shield for the substrate 12 during spinning. Between the locking members and the studs, a plurality of channels 50, 52, 54, 56, 58 and 60 are disposed, which are used to remove excess blood and/or diluent. To further assist in the removal of the excess blood and/or diluent, a plurality of holes 61 are formed in the substrate holder 10. Optionally, the ends of the planar surface 16 can be further cut out so as to allow the substrate 12 to lie flat, while having an adhesive label applied to one end of the substrate 12. Also, a circular center cut-out can be positioned on the rotational axis 18 to provide a visual indication of where to apply the blood sample.

FIG. 3 is shown to illustrate some possible design variations to the slide holder 10. For the purposes of clarity and understanding, the slide holder 10 is defined to have a longitudinal axis 62 and four sections or quadrants 64, 66, 68 and 70 defined by dashed illustration lines 71 and the longitudinal axis 62. The planar surface 16 defines a slide containing portion of the base portion 14, with the locking members surrounding this slide containing portion. Typically, the substrate 12 (not shown in FIG. 3) has the dimensions of 1 inch by 3 inches, i.e., generally has a rectangular configuration. Hence, in the preferred arrangement, one of the four locking members 20 through 26 are positioned in each of the quadrants 64 through 70, so as to define geometric rectangle 72 with a locking member at each corner thereof. For the purpose of illustration, the rectangle 73 defines the periphery of the quadrants. Moreover, the first pair of locking members 20 and 22 are positioned on a first diagonal line 74 of the rectangle 72 and the second pair of locking members 24 and 26 are positioned on a second diagonal line 76 of the rectangle 72, with each diagonal line 74 and 76 passing through the rotational axis 18, which is also the geometric center axis of the slide holder 10. Preferably, but not necessarily, the spacing between the rotational axis 18 and each of the locking members, taken along the two diagonal lines 74 and 76, are all the same. If this spacing varies for one or more of the locking members on a given diagonal line, then weight might have to be added to or subtracted from the locking members or other adjoining structure to balance the slide holder. Regardless of the positioning of the locking members along the longer sides of the slide holder 10, the locking members will be equally spaced from the longitudinal axis 62 of the slide holder 10. This equal spacing from the longitudinal axis 62 allows for the substrate 12 to be centered along its width dimensions with respect to the rotational axis 18. Additionally, the spacing from the inware facing extremities of the locking members to the longitudinal axis 62 is slightly greater than one-half of the width of the substrate, which allows for the substrate to be dropped in place, without tilting the substrate.

Although it is preferable to have all four of the locking members 20 through 26 to prevent the substrate 12 from flying loose from the slide holder 10 during spinning, the broadest scope of the invention encompasses using at least one locking member, for example during acceleration or deceleration. Alternatively, the use of only two adjacent locking members can be used to secure one end of the slide during both acceleration and deceleration. In both of these cases where less than the four locking members of the preferred embodiment are used, stop means in the form of, for example the ledges 46 and 48, can be used in the positions of the deleted locking members. The stop means prevent the substrate from sliding out of its alignment wherein the geometric axis of the substrate 12 is colinear with the rotational axis 18. The addition of each locking member provides added reliability in securing the substrate 12 during spinning, with the greatest reliability being provided by having all four locking members. Moreover, the positioning of the locking members with the same dimensions on the diagonal lines 74 and 76 reduces the need for balancing the slide holder 10. Also, by positioning the locking members toward the ends of the substrate 12, greater overhangs can be incorporated into the locking members, thereby providing better securement of the substrate 12.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A method of securing a substrate for spun blood smears in a substrate holder of a spinning apparatus comprising the steps of:
   loosely placing the substrate in the substrate holder;
   spinning of the substrate holder about its geometric axis by accelerating the substrate holder to a constant rotational speed of spinning and thereafter spinning the substrate at the constant rotational speed;

during acceleration of the substrate holder, employing the inertia of the substrate to slide at least one edge of the substrate under an inwardly-facing overhang portion of one of a pair of locking members to secure the substrate during the acceleration and the constant rotational speed spinning of the substrate holder;

decelerating the substrate holder from its constant rotational speed to a stationary disposition;

during deceleration of the substrate holder, employing the inertia of the substrate to slide the substrate away from said first engaged locking member so that at least one other edge of the substrate slides under an inwardly-facing overhang portion of the other said locking member of said first pair to secure the substrate during the deceleration of the substrate holder.

2. The method according to claim 1, wherein said step of employing inertia during acceleration includes sliding a first pair of diagonally-positioned corners of the substrate under a pair of diagonally-positioned locking members and said step of employing inertia during deceleration includes sliding a second pair of diagonally-positioned corners of the substrate under a second pair of diagonally-positioned locking members.

3. The method according to claim 2, wherein said step of loosely placing the substrate comprises placing the substrate in the substrate holder without substantially tilting the substrate.

4. A substrate holder for a spinning apparatus wherein said substrate holder is spun substantially about its geometric axis to spread a blood sample on a substrate, said substrate holder comprising:

a mounting base having a substrate containing portion adapted to support the substrate, said substrate containing portion being substantially centered on the geometric axis of said substrate holder, said substrate containing portion having two perpendicular axes which substantially orthogonally pass through said geometric axis and divide said substrate containing portion into four quadrants;

a first pair of locking members being mounted on said mounting base, each of said locking members being substantially adjacent a different one of two of said quadrants, with said two quadrants contiguously positioned to have a common boundary of one of said perpendicular axes;

each said locking member includes an inwardly-facing overhang portion disposed in extending relationship over said substrate containing portion and designed for having the substrate slide thereunder to secure the substrate when the spinning of said substrate holder pivots the substrate into one of said locking members, one of said locking members of said first pair being operative to secure the substrate during acceleration and the other said locking member of said first pair being operative to secure the substrate during deceleration;

said substrate containing portion being of sufficient dimensions and size to allow for the initial loose placement of the substrate therein without the securing engagement of the substrate with said locking members; and stop means associated with said substrate containing portion to prevent said substrate from sliding therefrom.

5. The substrate holder according to claim 4, wherein said stop means is adjacent to each of said quadrants not having one of said locking members.

6. The substrate holder according to claims 4 or 5, wherein that part of said substrate portion not obstructed by said locking members is of sufficient dimensions and size to allow for the initial loose placement of the substrate therein without having to tilt the substrate.

7. The substrate holder according to claim 4, further including, a second pair of locking members being mounted on said mounting base substantially adjacent the two said quadrants not having said locking members of said first pair, each said locking member of said second pair including an inwardly-facing overhang portion disposed in extending relationship over said substrate containing portion and designed for having the substrate slide thereunder; and one diagonally-positioned pair of said locking members being operative to secure the substrate during acceleration and the other diagonally-positioned pair of said locking members being operative to secure the substrate during deceleration, whereby each said quadrant has a locking member for securing an edge of the substrate.

8. The substrate holder according to claim 7, wherein said substrate containing portion has an elongated configuration defining one of said perpendicular axis to be a long axis and the other said perpendicular axis to be a short axis.

9. The substrate holder according to claim 8, wherein each of said locking members has the inward-facing extremity of its overhang portion substantially equally spaced from said long axis by a distance slightly greater than one-half of the width of the substrate, whereby the substrate can be placed in said substrate containing portion without tilting.

10. The substrate holder according to claim 9, wherein said substrate portion is generally rectangular and one of said locking members is disposed in each corner of a rectangle, said rectangle being centered on said geometric axis of said substrate holder.

* * * * *